United States Patent [19]
Chu et al.
[11] Patent Number: 5,041,374
[45] Date of Patent: Aug. 20, 1991

[54] POLYETHER ANTIBIOTIC RECOVERY AND PURIFICATION

[75] Inventors: Alexander H. T. Chu; Robert J. Urban, both of Terre Haute, Ind.
[73] Assignee: International Minerals & Chemical Corp., Northbrook, Ill.

[21] Appl. No.: 868,015
[22] Filed: May 29, 1986
[51] Int. Cl.[5] ........................ C12P 17/16; C12P 17/18; C12N 1/38; C07D 407/00
[52] U.S. Cl. .................................... 435/111; 435/119; 435/886; 435/244; 549/414
[58] Field of Search ............ 435/118, 170, 886, 253.5, 435/803, 244, 119; 424/123; 549/414

[56] References Cited

U.S. PATENT DOCUMENTS

| | | | |
|---|---|---|---|
| 3,326,775 | 6/1967 | Miescher | 195/47 |
| 3,929,575 | 12/1975 | Miescher | 195/30 |
| 3,995,027 | 11/1976 | Gale et al. | 424/115 |
| 4,009,262 | 2/1977 | Boeck et al. | 424/123 |
| 4,033,823 | 7/1977 | Liu et al. | 195/80 R |
| 4,035,481 | 7/1977 | Berg et al. | 424/122 |
| 4,038,384 | 7/1977 | Berg et al. | 424/122 |
| 4,085,224 | 4/1978 | Berg et al. | 424/283 |
| 4,110,435 | 8/1978 | Nakatsukasa et al. | 424/122 |
| 4,110,436 | 8/1978 | Nakatsukasa et al. | 424/122 |
| 4,137,241 | 1/1979 | Liu et al. | 260/345.7 |
| 4,141,907 | 2/1979 | Nakatsukasa et al. | 260/345.7 |
| 4,174,390 | 11/1979 | Hamill et al. | 424/117 |
| 4,174,404 | 11/1979 | Nakatsukasa et al. | 424/283 |
| 4,204,039 | 5/1980 | Nakatsukasa et al. | 435/118 |
| 4,212,942 | 7/1980 | Miyazaki et al. | 435/119 |
| 4,214,091 | 7/1980 | Oishi et al. | 549/62 |
| 4,221,724 | 9/1980 | Liu et al. | 260/345.8 |
| 4,263,427 | 4/1981 | Liu et al. | 536/1 |
| 4,265,028 | 5/1981 | Nakamura et al. | 435/118 |
| 4,288,493 | 8/1981 | Liu et al. | 435/119 |
| 4,294,925 | 10/1981 | Liu et al. | 435/84 |
| 4,395,491 | 7/1983 | Hohl et al. | 435/262 |
| 4,440,857 | 4/1984 | Seno et al. | 435/118 |

OTHER PUBLICATIONS

Lehninger, A., Biochemistry, 1982, Worth, p. 303.
Stark et al., *Antimicrob. Agents and Chemotherapy* 1967, pp. 353-358.
Ralston, A. W., *Fatty Acids and Their Derivatives* pp. 281-289, 1948, Wiley and Sons.
Morrison et al., *Organic Chemistry*, pp. 1059-1061, 1980, Allyn and Bacon.

*Primary Examiner*—Douglas W. Robinson
*Assistant Examiner*—Irene Marx
*Attorney, Agent, or Firm*—Wendell R. Guffey; Thomas L. Farquer

[57] ABSTRACT

Polyether antibiotic material is liberated from agglomerates containing a lipid material and the polyether antibiotic material by separating the polyether antibiotic from the lipid through formation of an acid salt of the lipid and a desired acid salt of the polyether antibiotic. The agglomerates can be formed during fermentation or produced by adding lipids afterwards.

21 Claims, No Drawings

POLYETHER ANTIBIOTIC RECOVERY AND PURIFICATION

BACKGROUND OF THE INVENTION

1. Field of the Invention

The present invention relates to a method for preparing a polyether antibiotic.

2. Description of the Background Art

Polyether antibiotics can be generally characterized as carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this class of antibiotics is set forth in Westley, *Adv. Appl. Microbiology,* 22:177–223 (1977). At least twenty different polyether antibiotics were known at the time the Westley article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyether antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin.

Class 1b of the polyether antibiotics are defined by Westley as monovalent monoglycoside polyether antibiotics. These polyether antibiotics, as the class name suggests, include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures. Included within class 1b are the polyether antibiotics septamycin, dianemycin, A-204, lenoremycin, carriomycin and etheromycin.

Class 2a as defined by Westley is directed to divalent polyether antibiotics. These antibiotics have a generally linear configuration, may contain from about two to about three tetrahydropyran and/or -furan structures, up to about three total ring structures and no nitrogen atoms. Included within class 2a are the antibiotics lasalocid and lysocellin.

Westley's class 2b of polyether antibiotics is directed to divalent pyrrole ethers and thus, in contrast to the antibiotics of the other classes, the class 2b antibiotics contain one or more nitrogen atoms. Included within class 2b are the polyether antibiotics X-14547, and A-23187 also known as calcimycin.

Polyether antibiotics are generally produced by fermenting a nutrient-containing liquid fermentation medium or broth inoculated with a microorganism capable of producing the desired antibiotic. Suitable liquid fermentation media are generally aqueous dispersions containing sources of assimilable nitrogen and carbon as is known in the art. The fermentation media can also contain a variety of optional ingredients, if desired, such as for example, pH adjustment agents, buffers, trace minerals, antifoam agents, and the like.

Known methods for recovering polyether antibiotics from fermentation broths generally involve complicated and expensive multi-stage solvent extractions and related filtration, chromatography, concentration, and crystallization operations. For example, the procedure to isolate and purify lysocellin first described by Ebata et al. used acetone, n-butanol and methanol (Ebata et al., *J. Antibiotics,* 28:118–121 (1975)). U.S. Pat. No. 4,033,823 describes an extraction process involving ethyl acetate, acetonitrile, hexane and methanol for recovering lysocellin. Commonly owned U.S. Pat. No. 4,478,935 describes various purified manganese-containing antibiotic complexes extracted from the dried biomass using suitable organic solvents followed by crystallization or precipitation of the complexes. All of these processes follow a rather standard approach in which fermentation broths are subjected to organic solvent extraction to recover the polyether antibiotics. The isolation and purification of polyether antibiotics using extraction methods have been extensively reviewed in Hamill et al., "Polyether Antibiotics" pp. 479–520, *J. Chromatogr. Lib.,* Vol. 15. Antibiotics: Isolation, Separation, and Purification, ed. by Weinstein, M. J. and Wagman, G. H. (1978).

There remains a need in the art for a method for preparing polyether antibiotic material without the need for complicated and expensive multi-stage solvent extractions and related filtration, chromatography, concentration and crystallization operations and the like.

SUMMARY OF THE INVENTION

In accordance with the present invention, a method for recovering and purifying a polyether antibiotic material comprises liberating polyether antibiotic from agglomerates containing a lipid material and said polyether antibiotic by separating said polyether antibiotic from said lipid material through formation of an acid salt of the lipid material and a desired acid salt of the polyether antibiotic.

DETAILED DESCRIPTION OF THE PREFERRED EMBODIMENTS

Polyether antibiotic materials generally are obtained by cultivating a polyether antibiotic-producing microorganism in a fermentation broth wherein the lipophilic polyether antibiotic is secreted into the aqueous fermentation medium. For example, the polyether antibiotic lysocellin can be produced by cultivating a lysocellin-producing strain of Streptomyces.

BEST AVAILABLE COPY

The present invention is applicable to agglomerates formed between polyether antibiotic material and a saponifiable lipid. The agglomerates (or aggregates) can be formed by producing a polyether antibiotic through cultivation of a polyether antibiotic-producing microorganism in a generally aqueous fermentation broth under conditions wherein at the end of fermentation sufficient lipid is present in the fermentation broth to form discrete agglomerates with polyether antibiotic in the fermentation broth. As fermentation proceeds, polyether antibiotic accumulates in the broth, and it has been found that if a lipid is present in the medium, the polyether antibiotic is attracted to the lipid due to the lipophilic nature and water insolubility of the polyether antibiotic. If, at the end of fermentation, sufficient lipid is present in the fermentation broth, agglomerates in the form of separable paste or pellets will form between the lipid and polyether antibiotic.

For growth of the microorganism and production of polyether antibiotic, a fermentation broth contains assimilable sources of carbon and nitrogen, and may contain trace elements and other optional ingredients, as is known in the art. The lipid with which agglomerates are formed can be assimilable source of carbon for the microorganism.

Examples of lipids with which agglomerates can be formed with polyether antibiotics include glyceride fats and oils, free fatty acids, and phospholipids such as lecithin. If during fermentative production of the polyether antibiotic, a principal carbon source other than a lipid is used, or the carbon source is depleted at the end of fermentation, it may be necessary to add sufficient lipid at or near the end of fermentation in order to form agglomerates. Advantageously, at least a portion of the principal carbon source during fermentation comprises the lipid.

An assimilable source of nitrogen is also provided in the culture medium. Suitable sources of nitrogen include yeast, yeast-derivated products, enzyme-hydrolyzed caseine, peptones, cornmeal, soybean meal, cottonseed meal, amino acids such as glutamic acid, and the like.

Nutrient inorganic salts can also be incorporated in the culture medium such as soluble salts capable of yielding sodium, magnesium, calcium, ammonium, chloride, carbonate, sulfate, nitrate, and like ions. Essential trace elements necessary for the growth and development of the microorganism should also be included in the culture medium. Such trace elements commonly occur as impurities in other constituents of the medium in amounts sufficient to meet the growth requirements of the organism.

Polyether antibiotics are produced by growing the polyether antibiotic-produced microorganism in an aerated, agitated, submerged culture with the pH of the broth adjusted to about neutral, i.e., from about 6.5 to about 7.5. Fermentation can generally be carried out at slightly elevated temperatures, e.g., between about 25° C. and 35° C. Incubation of the broth can be carried out for a period of several days, e.g., from about 4 to 12 days or longer if it is economically advantageous to do so.

It may be necessary to add small amounts (i.e., 0.2 ml/l) of an anti-foam agent such as polypropylene glycol to large-scale fermentation media if foaming becomes a problem. Excessive foaming may occur, for example, when fatty acids are added initially to the fermentation broth as the principal carbon source.

In one embodiment, the lipid which forms agglomerates with polyether antibiotic is comprised of glycerides, fatty acids or a mixture thereof. Suitable glycerides include soybean oil, safflower oil, cottonseed oil, sesame oil, olive oil, rape oil, peanut oil, corn oil, sunflower oil and like vegetable oils, cod oil and like fish oils, and lard and like animal-fat-and-oils. Vegetable oils are preferred glycerides, with soybean oil being particularly preferred.

Suitable free fatty acids for forming agglomerates with polyether antibiotics with or without glycerides include saturated fatty acids such as lauric acid, myristic acid, palmitic acid, stearic acid, arachidic acid, lignoceric acid and the like, and unsaturated fatty acids such as palmitoleic acid, oleic acid, linoleic acid, linolenic acid, arachidonic acid and the like. Unsaturated fatty acids are preferable, with oleic acid being most preferred.

A respective ratio by weight of polyether antibiotic to lipid in the fermentation broth of about 1:2 or greater will generally produce separable agglomerates in the form of semi-solid paste or pellets. If the ratio by weight of polyether antibiotic to lipid is less than about 1:2, the resulting oily mass containing accrued polyether antibiotic tends to clog screens and is difficult to separate from the balance of the fermentation broth.

According to one embodiment, the respective ratio by weight of polyether antibiotic to lipid in the fermentation broth at the end of fermentation is from about 1:2 to about 3:1. Generally, if the ratio of polyether antibiotic to lipid is greater than about 3:1 by weight, separable agglomerates will form between the available lipid and polyether antibiotic, but non-aggregated polyether antibiotic will remain in the fermentation broth due to an insufficient amount of lipid, making recovery of the non-aggregated antibiotic material difficult.

If at the end of fermentation the respective ratio by weight of polyether antibiotic to lipid in the fermentation broth is from about 1:1 to about 2:1, the resulting agglomerates take the form of solid or semi-solid pellets or beads ranging in size from about 3 mm to about 10 mm which may easily be separated from the broth using a coarse screen (e.g., U.S. standard series No. 35). If desired, the separated agglomerates can be washed with water to further cleanse the material.

During fermentation, the fermentation broth advantageously contains as a principal carbon source a mixture of free fatty acids and glycerides, most preferably a mixture of oleic acid and soybean oil. Desirably, the respective ratio by weight of oleic acid to soybean oil during at least a portion of fermentation is from about 4:1 to about 1:1.

Free fatty acids, such as oleic acid, are much more quickly metabolized during fermentation as compared to glyceride oils, but are generally quite toxic to microorganisms except at low concentrations. Free fatty acids can thus advantageously be used to obtain higher antibiotic yields or titers by continuously feeding low concentrations of free fatty acids to the broth during fermentation at about a rate at which the free fatty acids are metabolized. If free fatty acids are used alone during fermentation as principal carbon source and are depleted at the end of fermentation, accruing crystals of polyether antibiotic are freely suspended in the fermentation broth and do not form agglomerates. Addition of at least a small amount of glycerides with free fatty acids during fermentation, which is preferably fed on a continuous basis to the on-going fermentation, can result in sufficient glycerides being present in the broth to facilitate the formation of agglomerates.

Advantageously, the free fatty acids are fed to the broth in combination with glycerides during fermentation. For example, oleic acid and soybean oil are fed in a respective ratio by weight of from about 4:1 to about 1:1 to the fermentation broth to achieve and maintain an oleic acid concentration in the fermentation broth of from about 0.1% to about 0.4% by weight during fermentation. The free fatty acids and glycerides are fed to the broth during fermentation until the desired concentration of lysocellin in the fermentation broth is achieved, e.g., generally in about 10–12 days.

At the end of fermentation, e.g., during the last 24 hours of fermentation, a respective ratio by weight of polyether antibiotic to lipid in the broth of about 1:2 or greater is achieved to form agglomerates which are separable from the broth. If excess lipids are present in the broth during the final stages of fermentation, lipid addition to the broth is terminated until sufficient lipids have been metabolized to achieve the desired ratio. If insufficient lipids are present in the broth towards the end of fermentation, additional lipids may be added. The resulting agglomerates can be separated from the balance of the fermentation broth by screening as noted above.

If no agglomerates are formed during fermentation, an additional oil agglomeration step in a mixing tank can also produce oil/antibiotic aggregates by adding appropriate amount of lipids, e.g., soybean oil, oleic acid, corn oil, olive oil and the like. The optimum ratio for water dilution is from about 1:1 to about 1:3, the weight percentage for the added lipids is from about 0.5% to about 5%, and the mixing time is from about 30 minutes to about 5 hours. The resulting agglomerates contain about 20% to about 70% lysocellin at a step yield of about 30% to about 99%. Addition of air is also beneficial to promoting agglomerate formation and flotation to separate the agglomerates from the medium containing cell debris and/or mycelium impurities. This lipophilic nucleation/aggregation process is operated preferably at pH of about neutral (6–7) and at ambient temperature; no other modifiers or additives are needed. The optimum agglomeration conditions may depend on the fermentation broth consistency and the original microorganism strain.

For recovery of the polyether antibiotic from the agglomerates, the agglomerates are mixed with water several times to remove residual aqueous broth, cell debris, and/or mycelia. The clean agglomerates are then added to an aqueous solution with base (e.g., 2% NaOH (aq) or KOH (aq)) to achieve and maintain a pH of about 10 or higher, in order to form an acid salt of the lipid and liberate the polyether antibiotic as an insoluble acid salt. At the same time, free acid or other salts of the polyether antibiotic can be converted to the desired salt form of the product, e.g., sodium salt with NaOH, potassium salt with KOH. Preferably, the aqueous medium has a weight of from about 5 to about 20 times that of said agglomerates, and the pH is raised to about 12–14 by NaOH addition. In order to facilitate rapid formation of acid salts of the lipids present in the agglomerates, the solution containing agglomerates and NaOH is advantageously agitated for from about 1 to about 5 hours to substantially form said salts of the lipids to liberate the insoluble polyether antibiotic salts.

The insoluble polyether antibiotic material then is isolated, e.g., by centrifugation or filtration, from the aqueous soap solution. The wet solids are reslurried several times into water to further remove residual base and lipid salts. The solution can be dewatered by solid-liquid separation, e.g., centrifugation or filtration, to isolate lysocellin solids, which are then dried in a vacuum oven or tumble drier to obtain the final product. This process has been utilized to obtain lysocellin purities for dried solids obtained directly from the soap solution in the range of from about 70–99%. Optionally, additional hexane washes can be utilized to improve the purities to 95–99% without significantly decreasing recoveries, since the solids from the NaOH solution generally contain more than 90% of the desired sodium salt of lysocellin which is essentially insoluble in hexane. Additional sodium conversion is possible for the crude lysocellin crystals when mixed with caustic in methanol. The crude lysocellin crystals can also be dissolved into methanol, ethanol and the like, to filter off the insoluble impurities, e.g., mycelia and cell debris.

The present invention can be utilized to prepare a polyether antibiotic material of high purity without the need for complicated and expensive multi-stage solvent extractions and related filtration, chromatography, concentration and crystallization operations.

The invention is further illustrated by the following examples which is not intended to be limiting.

EXAMPLE I

Seed Development

Capsules of seed culture of a lysocellin-producing strain of *S. cacaoi var. asoensis* containing 1 ml of culture in glycerol were stored at −80° C. The content of one capsule was added to 80 ml first stage inoculum medium in a 500 ml Erlenmeyer flask. The medium contained (in wt. %) glycerol (2%), Bacto Peptone (1%), Bacto Meat Extract (1%), and tap water to volume. The flask was incubated on a rotary action shaker (~350 rpm) at 28°–30° C. for 48 hours (until satisfactory growth was established), and this seed was used immediately to inoculate the second stage inoculum as follows.

2.5 Percent of the first stage inoculum was added to 100 ml second stage inoculum medium in each of several 500 ml Erlenmeyer flasks. The medium contained (by wt. %) soybean oil (2.5%), soybean flour (2.5%), $KH_2PO_4$ (0.15%), $K_2HPO_4$ (0.15%), and the trace elements $FeSO_4 \cdot 7H_2O$ (5 ppm), $MnSO_4 \cdot H_2O$ (1.5 ppm), $CoCl_2 \cdot 6H_2O$ (0.5 ppm), and distilled water. The flasks were incubated on rotary action shakers (~350 rpm) at 28°–30° C. for about 24 hours. The second stage inoculum was transferred immediately from shaker to fermenter.

EXAMPLE II

Main Fermentation

In separate fermentations, 200 milliliters from 2 flasks of the second stage inoculum were used (~2% wt.) to inoculate a 20-liter sterilized fermenter containing (by wt. %) as "standard" principal medium soybean flour (4.5%), soybean oil (3%), $KH_2PO_4$ (0.05%), $K_2HPO_4$ (0.15%), and $CoCl_2 \cdot 6H_2O$ (1 ppm). Hodag K-67 antifoam (about 0.1%) and tap water to about a 10 liter volume. The pH of the inoculated medium was about neutral and did not require any further pH adjustment.

The physical parameters for fermentations using a New Brunswick fermenter were as follows:

| | | |
|---|---|---|
| Medium, volume | 10,000 ml | |
| Air | 10 l/min | (5 l/min during first 16 hr) |
| PSI g | 4 | |
| Agitation | 2 impellers, 10.8 cm diam. | |
| RPM | 650 | |
| Temperature | 29-30° C. | |

Oleic acid alone, mixtures of oleic acid and soybean oil or soybean oil alone was fed into the various fermentation broths when the pH of the fermentations began to rise, indicating the development stage of the fermentation (about 15-20 h after inoculation). The feed rate was about 0.5% to 1.5% (wt.) per day to maintain an oleic carbon source concentration in the medium in the range between 0.1 and 0.4%.

The fermentation results are shown in Table 1 below, which indicates the feed mixture used, final lysocellin titers and agglomerate formation.

The above table demonstrates aggregate formation obtained according to the invention.

EXAMPLE III

A number of fermentation batches produced by Streptomyces type strains did not form any discrete oil droplets; the lysocellin crystals were well dispersed in the aqueous medium as observed by microscope. Six randomly selected experiments shown in Table 2 represent the batches produced by three different mutated strains from three different-size fermentors over a period of one year. Various glycerides, fatty acids, or mixtures thereof were used to selectively catch the lipophilic lysocellin crystals to form agglomerates outside fermentors. A wide range of amount of lipids (0.5-8%), dilution (1:3-1:5), mixing time (1-4.5 hours) was tested to recover lysocellin. The results are summarized in Table 2 which demonstrates that high yield (73-100%) can be achieved via oil agglomeration, thus significantly reducing the volume for downstream purification.

TABLE 1

Final Lysocellin Titers in Fermentation Using Various Feeding Combinations of Oleic Acid and Soy Oil

| Batch No. | Variation Medium | Final Lysocellin Titer g/l | Initial Soy Oil in Medium % | Feed Mixture Soy Oil % | Feed Mixture Oleic Acid % | Agglomerate Separation by Screening % Agglomerates | Agglomerate Separation by Screening % Filtrate |
|---|---|---|---|---|---|---|---|
| 100% Oleic Acid Fed | | | | | | | |
| 1 | a | 35 | 3 | 0 | 100 | very few agglomerates | |
| 2 | b | 29 | 3 | 0 | 100 | very few agglomerates | |
| 20% Soybean Oil/80% Oleic Acid Fed | | | | | | | |
| 3 | none | 29 | 3 | 20 | 80 | 80 | 20 |
| 4 | none | 26 | 3 | 20 | 80 | 91.5 | 8.5 |
| 5 | c | 36 | 3 | 20 | 80 | 88 | 12 |
| 30% Soybean Oil/70% Oleic Acid Fed | | | | | | | |
| 6 | c | 29 | 3 | 30 | 70 | 91 | 9 |
| 40% Soybean Oil/60% Oleic Acid Fed | | | | | | | |
| 7 | none | 32 | 3 | 40 | 60 | 94 | 6 |
| 8 | none | 36 | 3 | 40 | 60 | 92 | 8 |
| 60% Soybean Oil/40% Oleic Acid Fed | | | | | | | |
| 9 | none | 31 | 3 | 60 | 40 | 96.3 | 3.7 |
| 100% Soybean Oil Used | | | | | | | |
| 10 | a | 19 | 7.5 | (no feed) | | 78 | 22 |
| 11 | a | 19 | 7.5 | (no feed) | | small oily beads - not screenable | |

a Medium contains soy flour (4.5%), soy oil (according to table), $KH_2PO_4$ (.1%), $K_2HPO_4$ (.2%), $CaCO_3$ (.4%), $FeSO_4.7H_2O$ (50 ppm), and $CoCl_2.6H_2O$ (2 ppm), with tap water.

b Medium contains soy flour (4.5%), soy oil (according to table), $KH_2PO_4$ (.05%), $K_2HPO_4$ (.15%), $CoCl_2.6H_2O$ (1 ppm), with tap water.

c Only variation from "standard" medium described above is 0.4% soy flour.

TABLE 2

Agglomeration with Various Lipids to Recover Lysocellin from Fermentation Broths Produced by Different Strains

| Batch No. | 1L | 9L | 25 | 17 | 49 | 49 |
|---|---|---|---|---|---|---|
| Strain | 1-15 | 1-15 | 4-1 | 4-1 | 4-2 | 4-2 |
| Titer (g/l) | 20 | 13 | 24 | 18 | 30 | 30 |
| Agglomerating Lipid | Oleic Acid[a] | Oleic Acid[a] | Oleic Acid/ Soybean Oil | Soyoil | Olive Oil | Corn Oil |
| Wt. % Lipid/Beer | 1.5% | 1.5% | 0.5%/0.5% | 8% | 5% | 4% |
| Dilution w/Water | 1:3 | 1:3 | 1:5 | 1:3 | 1:3 | 1:3 |
| Mixing Time (hr) | 2 | 1 | 1 | 4.5 | 3 | 3 |
| pH | 6-7 | 6-7 | 6-7 | 7 | 7 | 7 |
| % Lyso in Agglom. | 62.5[b] | 79.6 | 34.4[c] | 18.2 | 29.0 | 25.6 |
| % Oleate in Agglom. | 15 | 9.6 | 7.2 | <0.1 | 1.1 | 0.5 |

TABLE 2-continued

| Agglomeration with Various Lipids to Recover Lysocellin from Fermentation Broths Produced by Different Strains | | | | | | |
|---|---|---|---|---|---|---|
| | Batch No. | | | | | |
| | 1L | 9L | 25 | 17 | 49 | 49 |
| % Step Yield | 101.0 | 95.5 | 72.6 | 76.9 | 82.6 | 88.1 |

[a]Oleic acid (Emersol 221) contained 73% oleic, 8% linoleic, 3% myristoleic, 1% linolenic; 4% palmitic, 3% myristic, and traces of lauric and stearic acids.
[b]Acid salt formation (pH = 12 for two hours) gave 93.5% final purity, 99.9% purity with the agglomerates free of mycelio. (obtained by use of air).
[c]Acid salt formation (pH = 12 for three hours) gave 88.3% final purity.

EXAMPLE IV

For fermentation broths not containing lysocellin loaded oil droplets, agglomeration with corn oil was found to be able to recover a significant amount of lysocellin from the aqueous medium. The resulting corn oil agglomerates appeared to respond well to 2% caustic solution to obtain good-purity product. Table 3 shows the results from the combined agglomeration and acid salt formation experiments under different operating conditions. The high overall yields of purified lysocellin from corn oil agglomerates manifest the advantages of the invention.

TABLE 3

| Yields with Corn Oil Agglomeration and Acid Salt Formation Process for Batches Not Containing Discrete Oil Droplets | | | |
|---|---|---|---|
| | Batch No. | | |
| | 18 | 68 | 34 |
| Oleic/Soyoil Feed | 100/0 | 80/20 | 100/0 |
| Titer (g/l) | 18 | 29 | 26 |
| Oil Agglomeration | | | |
| Wt. % Corn Oil Added | 3 | 2.5 | 1 |
| Dilution w/Water | 1:3 | 1:1 | 1:1 |
| Mixing Time (hr) | 3 | 5 | 3 |
| % Lyso in Agglom. | 33.4 | 50.7 | 58.2 |
| % Agglom. Step Yield | 99+ | 84.8 | 88.2 |
| Acid Salt Formation | | | |
| 2% NaOH/Agglom. (w/w) | 1:10 | 1:20 | 1:20 |
| Rection Time (hr) | 5 | 5 | 5 |
| % Lyso Purity in Dried Product | 86.1 | 95.0 | 86.6 |
| % Step Yield | 72.3 | 79.4 | 89.9 |
| % Overall Recovery | 72.3 | 67.3 | 79.3 |
| % Overall Mass Balance | 74.5 | 87.0 | 91.0 |

EXAMPLE V

Agglomerates from batches 4, 5, 6, 7 and 8 of Example II were washed in tap water and subject to caustic treatment in 2% NaOH for three hours. The caustic mixture was centrifuged to separate lysocellin solids from the aqueous liquid containing water-soluble lipid salts. The wet solids were then reslurried into deionized water to further remove caustic and soap ingredients. The mixture was either centrifuged or filtered (vacuum or pressure) for dewatering. Two to three washes might be needed to obtain high purity. The results are summarized in Table 4 below, and demonstrate the advantages of the invention in providing high yields of purified lysocellin from agglomerates.

TABLE 4

| Yields with Acid Salt Formation Recovery Process for Batches Containing Fermentation-Produced Beads | | | | | | | | |
|---|---|---|---|---|---|---|---|---|
| Batch | Oleic Acid/ Soyoil Feed | Titer (g/l) | Beads/ Filtrate | % Lysocellin | % Purity (After NaOH) | Recovery | Yield | Effective Titer[c] |
| 4 | 80/20 | 26 | 91.5% (Beads)<br>8.5% (Filt.) | 68.0[a] (73.1%)[b]<br>0.21 | 99.9 | 88.1% | 81% | 21 |
| 7 | 60/40 | 32 | 94.0%<br>6.0% | (50.5%)[b] | 95.3 | 100.1% | 94% | 30 |
| 5 | 80/20 | 36 | 88%<br>12% | (74.3%)[b] | 99.8 | 86.3% | 76% | 27 |
| 6 | 70/30 | 29 | 91%<br>9% | (70.8%)[b] | 99.9 | 70.9% | 65% | 19 |
| 8 | 60/40 | 36 | 92%<br>8% | (81.5%)[b] | 96.6 | 85.4% | 79% | 28 |

[a,b]Lysocellin content in the beads before and after water wash.
[c]Effective titer = fermentation titer × overall yield.

What is claimed is:

1. A method for purifying a polyether antibiotic material comprising liberating polyether antibiotic from agglomerates containing a lipid material and said polyether antibiotic by separating said polyether antibiotic from said lipid material through formation of an acid salt of the lipid material and a desired acid salt of the polyether antibiotic.

2. The method of claim 1 wherein said lipids comprise glycerides, fatty acids or mixtures thereof.

3. The method of claim 2 wherein the polyether antibiotic material comprises lysocellin.

4. The method of claim 2 wherein the respective ratio by weight of polyether antibiotic to lipid in the agglomerates is from about 1:2 to about 3:1.

5. The method of claim 3 wherein the respective ratio by weight of polyether antibiotic to lipid in the agglomerates is from about 1:2 to about 3:1.

6. The method of claim 4 wherein said ratio is from about 1:1 to about 2:1.

7. The method of claim 5 wherein said ratio is from about 1:1 to about 2:1.

8. The method of claim 1 wherein said acid salt of said lipid is formed in an aqueous medium at a pH of the medium of about 10 or higher.

9. The method of claim 3 wherein said acid salt of said lipid is formed in an aqueous medium at a pH of the medium of about 10 or higher.

10. The method of claim 5 wherein said acid salt of said lipid is formed in an aqueous medium at a pH of the medium of about 10 or higher.

11. The method of claim 7 wherein said acid salt of said lipid is formed in an aqueous medium at a pH of the medium of about 10 or higher.

12. The method of claim 9 wherein said acid salt of said lipid is formed in the presence of aqueous NaOH or KOH.

13. The method of claim 10 wherein said acid salt of said lipid is formed in the presence of aqueous NaOH or KOH.

14. The method of claim 11 wherein said acid salt of said lipid is formed in the presence of aqueous NaOH or KOH.

15. The method of claim 12 wherein said aqueous medium has a weight of from about 5 to about 20 times that of said agglomerates.

16. The method of claim 13 wherein said aqueous medium has a weight of from about 5 to about 20 times that of said agglomerates.

17. The method of claim 14 wherein said aqueous medium has a weight of from about 5 to about 20 times that of said agglomerates.

18. The method of claim 15 wherein the pH of said medium is about 12-14, and said medium is agitated for a period of from about 1 to about 5 hours to substantially form said acid salt of said lipid, and to liberate the polyether antibiotic as an insoluble material, wherein insoluble polyether antibiotic material is thereafter isolated from the medium.

19. The method of claim 16 wherein the pH of said medium is about 12-14, and said medium is agitated for a period of from about 1 to about 5 hours to substantially completely form said acid salt of said lipid, and to liberate the polyether antibiotic as an insoluble material, wherein insoluble polyether antibiotic material is thereafter isolated from the medium.

20. The method of claim 17 wherein the pH of said medium is about 12-14, and said medium is agitated for a period of from about 1 to about 5 hours to substantially completely form said acid salt of said lipid, and to liberate the polyether antibiotic as an insoluble material, wherein insoluble polyether antibiotic material is thereafter isolated from the medium.

21. The method of claim 5 wherein the liberated polyether antibiotic is further purified by washing said polyether antibiotic with hexane.

* * * * *